United States Patent [19]

Elbe et al.

[11] Patent Number: 4,584,308

[45] Date of Patent: Apr. 22, 1986

[54] SUBSTITUTED HYDROXYALKYL-AZOLE FUNGICIDAL AGENTS, THEIR PREPARATION AND THEIR USE

[75] Inventors: Hans-Ludwig Elbe, Wuppertal; Karl H. Büchel, Burscheid; Wilhelm Brandes, Leichlingen; Paul Reinecke, Leverkusen; Hans-Jürgen Rosslenbroich, Monheim, all of Fed. Rep. of Germany

[73] Assignee: Bayer Aktiengesellschaft, Leverkusen, Fed. Rep. of Germany

[21] Appl. No.: 554,749

[22] Filed: Nov. 23, 1983

[30] Foreign Application Priority Data

Dec. 9, 1982 [DE] Fed. Rep. of Germany ....... 3245504

[51] Int. Cl.$^4$ .................... A01N 43/50; A01N 43/64; A01N 55/02; A01N 55/04
[52] U.S. Cl. ................................. 514/383; 514/184; 514/189; 514/399
[58] Field of Search ................... 424/245, 269, 273 R; 514/383, 399, 184, 189

[56] References Cited

U.S. PATENT DOCUMENTS 4,301,166 11/1981 Regel et al. ................. 424/269
4,381,306 4/1983 Regel et al. ................. 424/269

FOREIGN PATENT DOCUMENTS 0019189 11/1980 European Pat. Off. .
0029542 6/1981 European Pat. Off. .
54974 6/1982 European Pat. Off. .
0055833 7/1982 European Pat. Off. .
0061835 10/1982 European Pat. Off. .
2946956 6/1981 Fed. Rep. of Germany .
3018866 11/1981 Fed. Rep. of Germany .
2103210 2/1983 United Kingdom .

Primary Examiner—Allen J. Robinson
Attorney, Agent, or Firm—Sprung Horn Kramer & Woods

[57] ABSTRACT

A method of combating fungi which comprises to such fungi or to a fungus habitat a fungicidally effective amount of a substituted hydroxyalkyl-azole of the formula

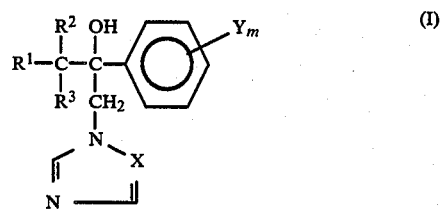

in which
$R^1$ is optionally substituted phenyl, —O-phenyl, —S-phenyl, —SO-phenyl, —SO$_2$-phenyl, —CH$_2$—phenyl, —CH$_2$—O-phenyl, —CH$_2$—S-phenyl, —CH$_2$—SO-phenyl or —CH$_2$—SO$_2$-phenyl,
$R^2$ is alkyl,
$R^3$ is alkyl,
X is a nitrogen atom or the CH group,
Y is halogen, alkyl, cycloalkyl, alkoxy, alkylthio, halogenoalkyl, halogenoalkoxy, halogenoalkylthio, optionally substituted phenyl, optionally substituted phenylalkyl or optionally substituted phenylalkoxy, and
m is 0, 1, 2 or 3, or an addition product thereof with an acid or metal salt.

10 Claims, No Drawings

SUBSTITUTED HYDROXYALKYL-AZOLE FUNGICIDAL AGENTS, THEIR PREPARATION AND THEIR USE

The present invention relates to the use of substituted hydroxyalkyl-azoles as fungicidal agents.

It has already been disclosed that certain hydroxyalkyl-azole derivatives have good fungicidal properties (compare DE-OS (German Published Specification) No. 2,920,375, U.S. application Ser. No. 144,104, filed Apr. 28, 1980, now abandoned, DE-OS (German Published Specification) No. 2,946,956 and DE-OS No. (German Published Specification) 3,018,866)).

However, the action of these compounds is not always completely satisfactory when low amounts and concentrations are applied.

It has been found that the substituted hydroxyalkyl-azoles of the general formula

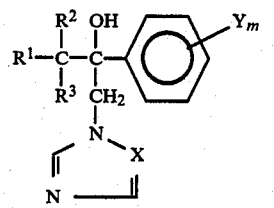

in which
R$^1$ represents in each case optionally substituted phenyl, —O—phenyl, —S—phenyl, —SO—phenyl, —SO$_2$—phenyl, —CH$_2$—phenyl, —CH$_2$—O—phenyl, —CH$_2$—S—phenyl, —CH$_2$—SO—phenyl or —CH$_2$—SO$_2$—phenyl,
R$^2$ represents alkyl,
R$^3$ represents alkyl,
X represents a nitrogen atom or the CH group,
Y represents halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl or optionally substituted phenylalkoxy and
m represents the number 0, 1, 2 or 3,
and acid addition salts and metal salt complexes thereof, have good fungicidal properties.

The compounds of the formula (I) have an asymmetric carbon atom and can therefore be obtained in the two optical isomer forms.

Surprisingly, the substituted hydroxyalkyl-azoles of the formula (I) to be used according to the invention exhibit a better fungicidal activity than the hydroxyalkylazolyl derivatives which are already known from the prior art and are closely related compounds structurally and from the point of view of their action. The use, according to the invention, of the new substances thus represents an enrichment of the art.

Formula (I) provides a general definition of the substituted hydroxyalkyl-azoles to be used according to the invention. Preferably, in this formula,
R$^1$ represents phenyl, —CH$_2$—phenyl, —CH$_2$—O—phenyl, —CH$_2$—S—phenyl, —CH$_2$—SO—phenyl or —CH$_2$—SO$_2$—phenyl, in each case mono- or di-substituted by identical or different substituents, preferred substituents on the phenyl which may be mentioned being the meanings of Y;
R$^2$ represents straight-chain or branched alkyl with 1 to 4 carbon atoms;
R$^3$ represents straight-chain or branched alkyl with 1 to 4 carbon atoms;
X represents a nitrogen atom or the CH group;
Y represents halogen, alkyl with 1 to 4 carbon atoms, cycloalkyl with 5 to 7 carbon atoms, alkoxy or alkylthio with in each case 1 to 4 carbon atoms, halogenoalkyl, halogenoalkoxy or halogenoalkylthio with in each case 1 to 2 carbon atoms and 1 to 5 identical or different halogen atoms, such as, preferably, fluorine and chlorine atoms, or phenyl, phenoxy or phenylalkyl or phenylalkoxy with 1 to 2 carbon atoms in the alkyl part or in the alkoxy part, each of which is optionally substituted by halogen or alkyl with 1 to 2 carbon atoms; and
m represents the number 0, 1, 2 or 3.

Moreover, preferably, in formula (I),
R$^1$ represents —O—phenyl, —S—phenyl, —SO—phenyl or —SO$_2$—phenyl, in each case mono- or di-substituted by identical or different substituents, preferred substituents on the phenyl which may be mentioned being the meanings of Y;
R$^2$ represents straight-chain or branched alkyl with 1 to 4 carbon atoms;
R$^3$ represents straight-chain or branched alkyl with 1 to 4 carbon atoms;
X represents a nitrogen atom or the CH group;
Y represents halogen, alkyl with 1 to 4 carbon atoms, cycloalkyl with 5 to 7 carbon atoms, alkoxy or alkylthio with in each case 1 to 4 carbon atoms, halogenoalkyl, halogenoalkoxy or halogenoalkylthio with in each case 1 or 2 carbon atoms and 1 to 5 identical or different halogen atoms, such as, preferably, fluorine and chlorine atoms, or phenyl, phenoxy or phenylalkyl or phenylalkoxy with 1 or 2 carbon atoms in the alkyl part or in the alkoxy part, each of which is optionally substituted by halogen or alkyl with 1 or 2 carbon atoms; and
m represents the number 0, 1, 2 or 3.

Particularly preferred compounds of the formula (I) are those in which
R$^1$ represents phenyl, —CH$_2$—phenyl, —CH$_2$—O—phenyl, —CH$_2$—S—phenyl, —CH$_2$—SO—phenyl or —CH$_2$—SO$_2$—phenyl, in each case mono- or di-substituted by identical or different substituents, preferred substituents on the phenyl which may be mentioned being the meanings of Y;
R$^2$ represents methyl or ethyl;
R$^3$ represents methyl or ethyl;
X represents a nitrogen atom or the CH group;
Y represents fluorine, chlorine, bromine, methyl, isopropyl, tert.-butyl, cyclohexyl, methoxy, methylthio, trifluoromethyl, trifluoromethoxy or trifluoromethylthio, or phenyl, phenoxy, benzyl or benzyloxy which is optionally substituted by fluorine, chlorine or methyl; and
m represents the number 0, 1 or 2.

Particularly preferred compounds of the formula (I) are, moreover, those in which
R$^1$ represents —O—phenyl, —S—phenyl, —SO—phenyl or —SO$_2$—phenyl, in each case mono- or di-substituted by identical or different substituents, preferred substituents on the phenyl which may be mentioned being the meanings of Y;
R$^2$ represents methyl or ethyl,
R$^3$ represents methyl or ethyl;

X represents a nitrogen atom or the CH group;

Y represents fluorine, chlorine, bromine, methyl, isopropyl, tert.-butyl, cyclohexyl, methoxy, methylthio, trifluoromethyl, trifluoromethoxy or trifluoromethylthio, or phenyl, phenoxy, benzyl or benzyloxy which is optionally substituted by fluorine, chlorine or methyl, and m represents the number 0, 1 or 2.

Addition products of acids and those substituted hydroxyalkyl-azoles of the formula (I) in which the substituents $R^1$, $R^2$, $R^3$, X and $Y_m$ have the meanings which have already been mentioned as preferred for these substituents are also preferred compounds according to the invention.

Preferred acids which can be added on include hydrogen halide acids, such as, for example, hydrochloric acid and hydrobromic acid, especially hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Addition products of salts of metals of main groups II to IV and of sub-groups I and II and IV to VIII and those substituted hydroxyalkyl-azoles of the formula (I) in which the substituents $R^1$, $R^2$, $R^3$, X and $Y_m$ have the meanings which have already been mentioned as preferred for these substituents are also preferred compounds according to the invention.

In this context, salts of copper, zinc, manganese, magnesium, tin, iron and nickel are particularly preferred. Suitable anions of these salts are those which are derived from acids leading to physiologically acceptable addition products. Particularly preferred acids of this type are, in this connection, the hydrogen halide acids, such as, for example, hydrochloric acid and hydrobromic acid, nitric acid and sulphuric acid.

The following compounds of the formula (I) may be mentioned specifically, in addition to the compounds mentioned in the preparation examples (X represents either a nitrogen atom or the CH group):

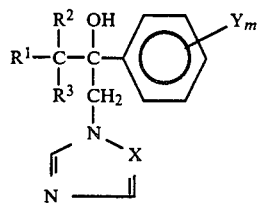

| $R^1$ | $R^2$ | $R^3$ | $Y_m$ |
|---|---|---|---|
| F—⟨⟩—O— | CH₃ | CH₃ | 2-Cl |
| (2-F)⟨⟩—O— | CH₃ | CH₃ | 2-Cl |
| Cl—⟨⟩—O— | CH₃ | CH₃ | 3-Cl |
| (2-Cl)⟨⟩—O— | CH₃ | CH₃ | 3,4-Cl₂ |
| (2-Cl)⟨⟩—O— | CH₃ | CH₃ | 3-Cl |
| Cl—⟨2-Cl⟩—O— | CH₃ | CH₃ | 3-Cl |
| Cl—⟨⟩—O— | CH₃ | CH₃ | 2,4-Cl₂ |
| F—⟨⟩—O— | CH₃ | CH₃ | 2,4-Cl₂ |
| Cl—⟨⟩—O— | CH₃ | CH₃ | 3,4-Cl₂ |
| Cl—⟨⟩—O— | CH₃ | CH₃ | 2-CH₃,4-Cl |
| F—⟨⟩—O— | CH₃ | CH₃ | 3,4-Cl₂ |
| F—⟨⟩—O— | CH₃ | CH₃ | 2-CH₃,4-Cl |
| Cl—⟨⟩—O— | CH₃ | CH₃ | 2-Cl |
| (2-Cl)⟨⟩—O— | CH₃ | CH₃ | 2-Cl |
| Cl—⟨2-Cl⟩—O— | CH₃ | CH₃ | 4-Cl |
| Cl—⟨2-Cl⟩—O— | CH₃ | CH₃ | 2,4-Cl₂ |
| Cl—⟨2-Cl⟩—O— | CH₃ | CH₃ | 2-Cl |
| Cl—⟨2-Cl⟩—O— | CH₃ | CH₃ | 4-F |

-continued $$\begin{array}{c} R^2 \quad OH \\ R^1-C-C-\phenyl-Y_m \\ R^3 \quad CH_2 \\ | \\ N-X \\ \| \\ N \end{array} \quad (I)$$

| $R^1$ | $R^2$ | $R^3$ | $Y_m$ |
|---|---|---|---|
| 2-Cl-C$_6$H$_4$-O— | CH$_3$ | CH$_3$ | 4-F |
| 4-Cl-C$_6$H$_4$-O— | CH$_3$ | CH$_3$ | 4-C$_6$H$_4$-Cl |
| 2-Cl-C$_6$H$_4$-O— | CH$_3$ | CH$_3$ | 4-C$_6$H$_4$-Cl |
| 2,4-Cl$_2$-C$_6$H$_3$-O— | CH$_3$ | CH$_3$ | 4-C$_6$H$_4$-Cl |
| 4-F-C$_6$H$_4$-O— | CH$_3$ | CH$_3$ | 4-C$_6$H$_4$-Cl |
| 4-Cl-C$_6$H$_4$-O— | CH$_3$ | CH$_3$ | 4-O-C$_6$H$_4$-Cl |
| 2-Cl-C$_6$H$_4$-O— | CH$_3$ | CH$_3$ | 4-Cl |
| 4-Cl-C$_6$H$_4$-O— | CH$_3$ | CH$_3$ | 2-F |
| 2-Cl-C$_6$H$_4$-O— | CH$_3$ | CH$_3$ | 2-F |
| 2,4-Cl$_2$-C$_6$H$_3$-O— | CH$_3$ | CH$_3$ | 2-F |
| 2-Cl-C$_6$H$_4$-O— | CH$_3$ | CH$_3$ | 2,4-Cl$_2$ |
| 2-F-C$_6$H$_4$-O— | CH$_3$ | CH$_3$ | 2,4-Cl$_2$ |
| 2-F-C$_6$H$_4$-O— | CH$_3$ | CH$_3$ | 4-Cl |
| 4-F-C$_6$H$_4$-S— | CH$_3$ | CH$_3$ | 2-Cl |
| 2-F-C$_6$H$_4$-S— | CH$_3$ | CH$_3$ | 2-Cl |
| 4-Cl-C$_6$H$_4$-S— | CH$_3$ | CH$_3$ | 3-Cl |
| 2-Cl-C$_6$H$_4$-S— | CH$_3$ | CH$_3$ | 3,4-Cl$_2$ |
| 2-Cl-C$_6$H$_4$-S— | CH$_3$ | CH$_3$ | 3-Cl |
| 2,4-Cl$_2$-C$_6$H$_3$-S— | CH$_3$ | CH$_3$ | 3-Cl |
| 4-Cl-C$_6$H$_4$-S— | CH$_3$ | CH$_3$ | 2,4-Cl$_2$ |
| 4-F-C$_6$H$_4$-S— | CH$_3$ | CH$_3$ | 2,4-Cl$_2$ |
| 4-Cl-C$_6$H$_4$-S— | CH$_3$ | CH$_3$ | 3,4-Cl$_2$ |
| 4-Cl-C$_6$H$_4$-S— | CH$_3$ | CH$_3$ | 2-CH$_3$,4-Cl |
| 4-F-C$_6$H$_4$-S— | CH$_3$ | CH$_3$ | 3,4-Cl$_2$ |
| 4-F-C$_6$H$_4$-S— | CH$_3$ | CH$_3$ | 2-CH$_3$,4-Cl |
| 4-Cl-C$_6$H$_4$-S— | CH$_3$ | CH$_3$ | 2-Cl |
| 2-Cl-C$_6$H$_4$-S— | CH$_3$ | CH$_3$ | 2-Cl |
| 2,4-Cl$_2$-C$_6$H$_3$-S— | CH$_3$ | CH$_3$ | 4-Cl |
| 2,4-Cl$_2$-C$_6$H$_3$-S— | CH$_3$ | CH$_3$ | 2,4-Cl$_2$ |

Formula (I)

Structure: R¹R³C(R²)−C(OH)(phenyl-Yₘ)−CH₂−N(X)−N=CH−CH= (triazole/imidazole ring with X)

| R¹ | R² | R³ | Yₘ |
|---|---|---|---|
| 2,4-dichlorophenyl-S− | CH₃ | CH₃ | 2-Cl |
| 2,4-dichlorophenyl-S− | CH₃ | CH₃ | 4-F |
| 2-chlorophenyl-S− | CH₃ | CH₃ | 4-F |
| 4-chlorophenyl-S− | CH₃ | CH₃ | 4-(4-Cl-phenyl) |
| 2-chlorophenyl-S− | CH₃ | CH₃ | 4-(4-Cl-phenyl) |
| 2,4-dichlorophenyl-S− | CH₃ | CH₃ | 4-(4-Cl-phenyl) |
| 4-fluorophenyl-S− | CH₃ | CH₃ | 4-(4-Cl-phenyl) |
| 4-chlorophenyl-S− | CH₃ | CH₃ | 4-O-(4-Cl-phenyl) |
| 2-chlorophenyl-S− | CH₃ | CH₃ | 4-Cl |
| 4-chlorophenyl-S− | CH₃ | CH₃ | 2-F |
| 2-chlorophenyl-S− | CH₃ | CH₃ | 2-F |
| 2,4-dichlorophenyl-S− | CH₃ | CH₃ | 2-F |
| 2-chlorophenyl-S− | CH₃ | CH₃ | 2,4-Cl₂ |
| 2-fluorophenyl-S− | CH₃ | CH₃ | 2,4-Cl₂ |
| 2-fluorophenyl-S− | CH₃ | CH₃ | 4-Cl |
| 4-fluorophenyl-CH₂− | CH₃ | CH₃ | 2-Cl |
| 2-fluorophenyl-CH₂− | CH₃ | CH₃ | 2-Cl |
| 4-chlorophenyl-CH₂− | CH₃ | CH₃ | 3-Cl |
| 2-chlorophenyl-CH₂− | CH₃ | CH₃ | 3,4-Cl₂ |
| 2-chlorophenyl-CH₂− | CH₃ | CH₃ | 3-Cl |
| 2,4-dichlorophenyl-CH₂− | CH₃ | CH₃ | 3-Cl |
| 4-chlorophenyl-CH₂− | CH₃ | CH₃ | 2,4-Cl₂ |
| 4-fluorophenyl-CH₂− | CH₃ | CH₃ | 2,4-Cl₂ |
| 4-chlorophenyl-CH₂− | CH₃ | CH₃ | 3,4-Cl₂ |
| 4-chlorophenyl-CH₂− | CH₃ | CH₃ | 2-CH₃,4-Cl |
| 4-fluorophenyl-CH₂− | CH₃ | CH₃ | 3,4-Cl₂ |
| 4-fluorophenyl-CH₂− | CH₃ | CH₃ | 2-CH₃,4-Cl |
| 4-chlorophenyl-CH₂− | CH₃ | CH₃ | 2-Cl |
| 2-chlorophenyl-CH₂− | CH₃ | CH₃ | 2-Cl |

-continued
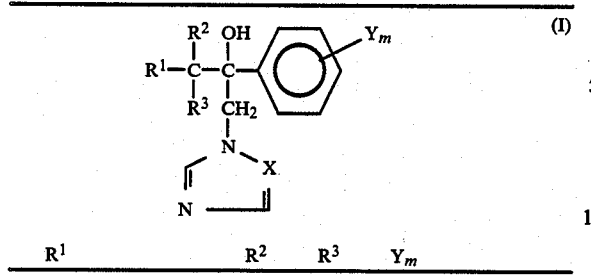
| R¹ | R² | R³ | $Y_m$ |
|---|---|---|---|
| 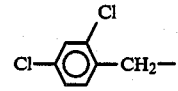 | CH₃ | CH₃ | 4-Cl |
| 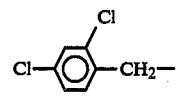 | CH₃ | CH₃ | 2,4-Cl₂ |
| 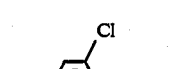 | CH₃ | CH₃ | 2-Cl |
| 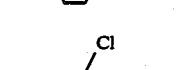 | CH₃ | CH₃ | 4-F |
| 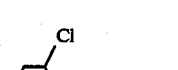 | CH₃ | CH₃ | 4-F |
| 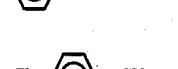 | CH₃ | CH₃ | 4-⟨○⟩-Cl |
| 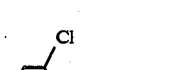 | CH₃ | CH₃ | 4-⟨○⟩-Cl |
| 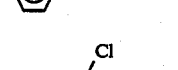 | CH₃ | CH₃ | 4-⟨○⟩-Cl |
| 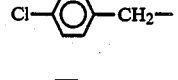 | CH₃ | CH₃ | 4-⟨○⟩-Cl |
| 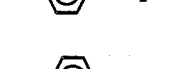 | CH₃ | CH₃ | 4-O-⟨○⟩-Cl |
| 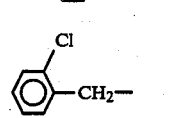 | CH₃ | CH₃ | 4-Cl |
|  | CH₃ | CH₃ | 2-F |
| 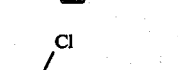 | CH₃ | CH₃ | 2-F |
| 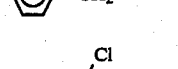 | CH₃ | CH₃ | 2-F |
-continued
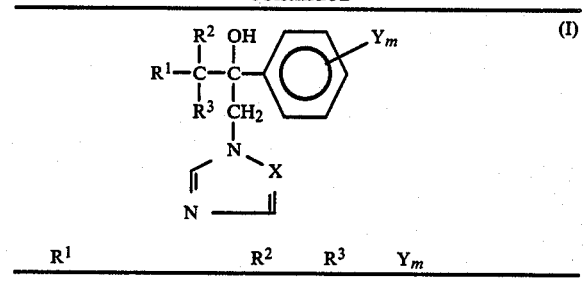
| R¹ | R² | R³ | $Y_m$ |
|---|---|---|---|
| 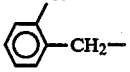 | CH₃ | CH₃ | 2,4-Cl₂ |
| 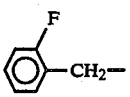 | CH₃ | CH₃ | 2,4-Cl₂ |
| 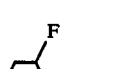 | CH₃ | CH₃ | 4-Cl |
| 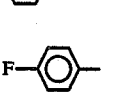 | CH₃ | CH₃ | 2-Cl |
| 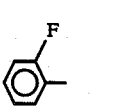 | CH₃ | CH₃ | 2-Cl |
|  | CH₃ | CH₃ | 3-Cl |
| 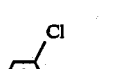 | CH₃ | CH₃ | 3,4-Cl₂ |
| 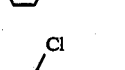 | CH₃ | CH₃ | 3-Cl |
| 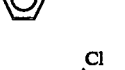 | CH₃ | CH₃ | 3-Cl |
| 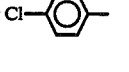 | CH₃ | CH₃ | 2,4-Cl₂ |
|  | CH₃ | CH₃ | 2,4-Cl₂ |
| 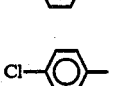 | CH₃ | CH₃ | 3,4-Cl₂ |
| 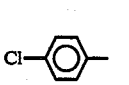 | CH₃ | CH₃ | 2-CH₃,4-Cl |
| 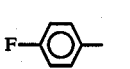 | CH₃ | CH₃ | 3,4-Cl₂ |
|  | CH₃ | CH₃ | 2-CH₃,4-Cl |

-continued $$\begin{array}{c} R^2 \ OH \\ R^1-C-C-\phantom{X}\!\!\!\!\!\!\!\!\!\!\!\!\bigcirc\!\!-Y_m \\ R^3 \ CH_2 \\ \phantom{xxx}| \\ \phantom{xxx}N-X \\ \phantom{xxx}\|\phantom{xx}\| \\ \phantom{xxxx}N== \end{array} \quad (I)$$

| R¹ | R² | R³ | Y_m |
|---|---|---|---|
| 4-Cl-C₆H₄- | CH₃ | CH₃ | 2-Cl |
| 2-Cl-C₆H₄- | CH₃ | CH₃ | 2-Cl |
| 2,4-Cl₂-C₆H₃- | CH₃ | CH₃ | 4-Cl |
| 2,4-Cl₂-C₆H₃- | CH₃ | CH₃ | 2,4-Cl₂ |
| 2,4-Cl₂-C₆H₃- | CH₃ | CH₃ | 2-Cl |
| 2,4-Cl₂-C₆H₃- | CH₃ | CH₃ | 4-F |
| 2-Cl-C₆H₄- | CH₃ | CH₃ | 4-F |
| 4-Cl-C₆H₄- | CH₃ | CH₃ | 4-(4-Cl-C₆H₄) |
| 2-Cl-C₆H₄- | CH₃ | CH₃ | 4-(4-Cl-C₆H₄) |
| 2,4-Cl₂-C₆H₃- | CH₃ | CH₃ | 4-(4-Cl-C₆H₄) |
| 4-F-C₆H₄- | CH₃ | CH₃ | 4-(4-Cl-C₆H₄) |
| 4-Cl-C₆H₄- | CH₃ | CH₃ | 4-O-(4-Cl-C₆H₄) |
| 2-Cl-C₆H₄- | CH₃ | CH₃ | 4-Cl |
| 4-Cl-C₆H₄- | CH₃ | CH₃ | 2-F |

-continued $$\begin{array}{c} R^2 \ OH \\ R^1-C-C-\phantom{X}\!\!\!\!\!\!\!\!\!\!\!\!\bigcirc\!\!-Y_m \\ R^3 \ CH_2 \\ \phantom{xxx}| \\ \phantom{xxx}N-X \\ \phantom{xxx}\|\phantom{xx}\| \\ \phantom{xxxx}N== \end{array} \quad (I)$$

| R¹ | R² | R³ | Y_m |
|---|---|---|---|
| 2-Cl-C₆H₄- | CH₃ | CH₃ | 2-F |
| 2,4-Cl₂-C₆H₃- | CH₃ | CH₃ | 2-F |
| 2-Cl-C₆H₄- | CH₃ | CH₃ | 2,4-Cl₂ |
| 2-F-C₆H₄- | CH₃ | CH₃ | 2,4-Cl₂ |
| 2-F-C₆H₄- | CH₃ | CH₃ | 4-Cl |

The active compounds to be used according to the invention are the subject of U.S. application Ser. No. 476,096, filed Mar. 17, 1983, now abandoned, and are obtained by a process in which oxiranes of the formula

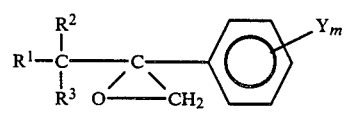

in which
R¹, R², R³, Y and m have the abovementioned meaning,
are reacted with azoles of the formula

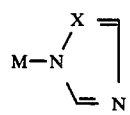

in which
X has the abovementioned meaning and
M represents hydrogen or an alkali metal, preferably sodium or potassium,
in the presence of an inert organic solvent, such as, for example, alcohols, and if appropriate in the presence of a base, such as, for example, alkali metal alcoholates, at temperatures between 60° and 150° C., and, if appropriate, the resulting hydroxyalkyl-azoles of the formula

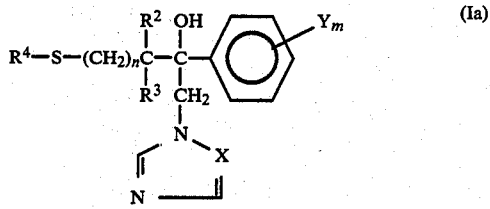

in which
R², R³, X, Y and m have the abovementioned meaning,
R⁴ represents optionally substituted phenyl and
n represents the number 0 or 1,
are oxidized by known methods in the customary manner.

If 1 mol of oxidizing agent, such as m-chloroperbenzoic acid in methylene chloride or hydrogen peroxide in acetic anhydride, is used at temperatures between −30° to +30° C., the compounds of the formula (I) according to the invention with the —SO— grouping are preferentially formed. With an excess of oxidizing agent and higher temperatures (10° to 80° C.), the compounds of the formula (I) according to the invention with the —SO₂— grouping are preferentially formed. The oxidation products are isolated in the customary manner.

The oxiranes of the formula (II) are also the subject of U.S. application Ser. No. 476,096, filed Mar. 17, 1983, now abandoned, and are obtained by a process in which ketones of the formula

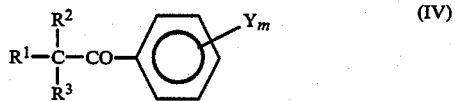

in which
R¹, R², R³, Y and m have the abovementioned meaning,
either
(α) are reacted with dimethyloxosulphonium methylide of the formula

in a manner which is in itself known, in the presence of a diluent, such as, for example, dimethylsulphoxide, at temperatures between 20° and 80° C. (in this context, compare the statements in J.Am.Chem.Soc. 87, 1363–1364 (1965)), or (β) are reacted with trimethylsulphonium methyl-sulphate of the formula

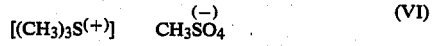

in a manner which is in itself known, in the presence of an inert organic solvent, such as, for example, acetonitrile, and in the presence of a base, such as, for example, sodium methylate, at temperatures between 0° and 60° C., preferably at room temperature (compare also the statements in Heterocycles 8, 397 (1977)).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The metal salt complexes of compounds of the formula (I) can be obtained in a simple manner by customary processes, thus, for example, by dissolving the metal salt in alcohol, for example ethanol, and adding the solution to the compounds of the formula (I). The metal salt complexes can be isolated in a known manner, for example by filtration, and if appropriate purified by recrystallization.

The active compounds to be used according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Dueteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Sphaerotheca species, such as against the powdery mildew of cucumber causative organism (*Sphaerotheca fuliginea*), cereal diseases, such as against the stripe disease of barley causative organism (*Drechslera graminea*) or against the brown spot disease on wheat causative organism (*Leptosphaeria nodorum*), and rice diseases, such as *Pyricularia oryzae* and *Pellicularia sasakii*.

When applied in appropriate amounts, the active compounds according to the invention also exhibit plant growth-regulating and selective herbicidal properties.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

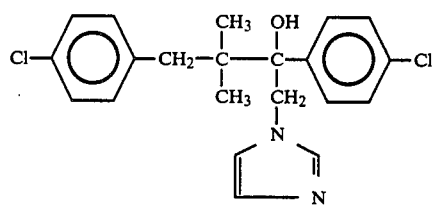

30 g (0.935 mol) of 2-(4-chlorophenyl)-2-(4-chlorophenyl-tert.-butyl)-oxirane in 40 ml of n-propanol are added dropwise to a solution of 7.7 g (0.108 mol) of sodium imidazole in 60 ml of n-propanol at the reflux temperature. The reaction mixture is subsequently stirred under reflux for 48 hours and cooled, water is added and the mixture is extracted with methylene chloride. The organic phase is dried over sodium sulphate and concentrated in vacuo. The oily residue is stirred into diisopropyl ether. The resulting crystalline precipitate is filtered off with suction and dried. 12.7 g (35% of theory) of 2,4-bis-(4-chlorophenyl)-3,3-dimethyl-1-(imidazol-1-yl)-2-butanol of melting point 174° C. are obtained.

Preparation of the starting substance

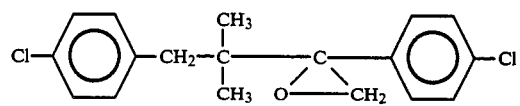

A solution of 59.2 g (0.47 mol) of dimethyl sulphate and 32 g (0.517 mol) of dimethyl sulphide in 270 ml of acetonitrile is stirred at room temperature for 5 days. A solution of 81.5 g (0.2655 mol) of 4-chlorophenyl 4-chlorophenyl-tert.-butyl ketone in 80 ml of acetonitrile is then added dropwise at 20° to 25° C. in the course of about 2 hours. 28.7 g (0.53 mol) of sodium methylate are added at the same temperature. The entire reaction mixture is subsequently stirred for 12 hours and is then concentrated in vacuo. The residue is stirred overnight with a mixture of 200 ml of ethyl acetate and 150 ml of water. The organic phase is separated off, dried over sodium sulphate and concentrated in vacuo. 72.6 g (85.2% of theory) of crude 2-(4-chlorophenyl)-2-(4-chlorophenyl-tert.-butyl)-oxirane are obtained and are further reacted directly.

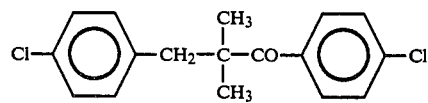

85 g (0.466 mol) of 4-chlorophenyl isopropyl ketone, 31.3 g (0.56 mol) of potassium hydroxide and 5 g of tetrabutylammonium bromide in 120 ml of toluene are heated to the reflux temperature, and a solution of 75 g (0.466 mol) of 4-chlorobenzyl chloride in 60 ml of toluene is added dropwise. The reaction mixture is subsequently stirred under reflux for 12 hours, cooled and washed with water and the organic phase is dried over sodium sulphate and concentrated in vacuo. 81.5 g (60% of theory) of 4-chlorophenyl 4-chlorophenyltert.-butyl ketone of refractive index $n_D^{20}$ 1.5711 are obtained.

EXAMPLE 2

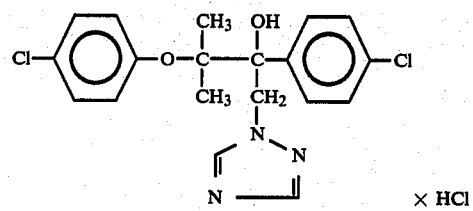 × HCl

A solution of 30 g (0.093 mol) of 2-(4-chlorophenyl)-2-[2-(p-chlorophenoxy)-prop-2-yl]-oxirane in 40 ml of n-propanol is added dropwise to a solution of 7.6 g (0.107 mol) of sodium 1,2,4-triazole in 60 ml of n-propanol at room temperature. The reaction mixture is subsequently stirred at the reflux temperature for 48 hours and is cooled, water is added and the mixture is extracted with methylene chloride. The organic phase is dried over sodium sulphate and concentrated in vacuo. The oily residue is purified by column chromatography. 6.7 g (18.4% of theory) of 3-(4-chlorophenoxy)-2-(4-chlorophenyl)-3-methyl-1-(1,2,4-triazol-1-yl)-2-butanol are obtained. This product is stirred with 20 ml of saturated hydrogen chloride/ether solution at room temperature. The precipitate which has separated out is filtered off with suction, rinsed with a little ether and dried at 40° C. in vacuo. 6.5 g (89% of theory, based on the base employed) of 3-(4-chlorophenoxy)-2-(4-chlorophenyl)-3-methyl-1-(1,2,4-triazol-1-yl)-2-butanol hydrochloride of melting point 135° C. are obtained.

Preparation of the starting substance

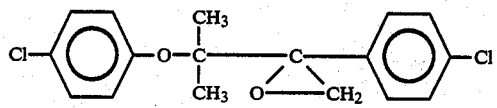

A solution of 59.2 g (0.47 mol) of dimethyl sulphate and 32 g (0.517 mol) of dimethyl sulphide in 270 ml of acetonitrile is stirred at room temperature for 5 days. A solution of 87 g of 4-chlorophenyl 2-(p-chlorophenoxy)-prop-2-yl ketone in 80 ml of acetonitrile is then added dropwise at 20° to 25° C. in the course of about 2 hours. 28.7 g (0.53 mol) of sodium methylate are introduced at the same temperature, and the mixture is subsequently stirred for 12 hours and then concentrated. The residue is stirred overnight with a mixture of 200 ml of ethyl acetate and 150 ml of water. The organic phase is separated off, dried over sodium sulphate and concentrated in vacuo. 49 g (76% of theory) of crude 2-(4-chlorophenyl)-2-[2-(p-chlorophenoxy)-prop-2-yl]-oxirane are obtained, and are further reacted directly.

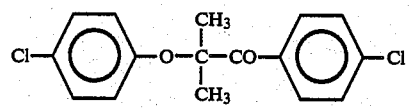

52 g (0.3982 mol) of p-chlorophenol and 55 g (0.3982 mol) of potassium carbonate in 400 ml of toluene are heated under reflux for 2 hours, using a water separator. The mixture is cooled to 40° C. and a solution of 2-bromo-prop-2-yl 4-chlorophenyl ketone in 170 ml of toluene is added dropwise. This reaction mixture is subsequently stirred at 100° C. for 5 hours and is then cooled, water is added and the organic phase is separated off. This phase is washed with dilute sodium hydroxide solution and water, dried over sodium sulphate and concentrated. 87 g (85% of theory) of crude 4-chlorophenyl 2-(p-chlorophenoxy)-prop-2-yl ketone are obtained and are further reacted directly.

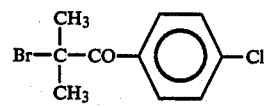

1 ml of hydrogen bromide/glacial acetic acid is added to 65.5 g (0.36 mol) of 4-chlorophenyl isopropyl ketone in 200 ml of chloroform, and 57.5 g (0.36 mol) of bromine are then added dropwise at 30° C. The mixture is subsequently stirred at room temperature for 30 minutes and is then concentrated in vacuo. 86.6 g (92% of theory) of crude 2-bromo-prop-2-yl 4-chlorophenyl ketone are obtained and are further reacted directly.

The following compounds of the general formula

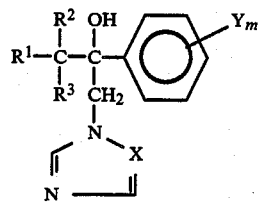

are obtained in a corresponding manner and according to the process described:

| Example No. | $R^1$ | $R^2$ | $R^3$ | X | $Y_m$ | Melting point (°C.) |
|---|---|---|---|---|---|---|
| 3 | Cl—⬡— | CH₃ | CH₃ | CH | 4-Cl | 138 |
| 4 | Cl—⬡—CH₂— | CH₃ | CH₃ | N | 4-Cl | 137 |
| 5 | Cl—⬡— | CH₃ | CH₃ | N | 4-Cl | 109 |
| 6 | ⬡—CH₂— | CH₃ | CH₃ | N | 4-F | 120 |
| 7 | ⬡—CH₂— | CH₃ | CH₃ | CH | 4-F | 118–120 |
| 8 | Cl—⬡—CH₂— | CH₃ | CH₃ | CH | 4-F | 165–167 |
| 9 | Cl—⬡—CH₂— | CH₃ | CH₃ | N | 4-F | 124 |
| 10 | F—⬡—CH₂— | CH₃ | CH₃ | CH | 4-Cl | 126 |

-continued

| Example No. | R¹ | R² | R³ | X | $Y_m$ | Melting point (°C.) |
|---|---|---|---|---|---|---|
| 11 | F-C₆H₄-CH₂- | CH₃ | CH₃ | N | 4-F | 112 |
| 12 | 2,3-Cl₂-C₆H₃-CH₂- | CH₃ | CH₃ | CH | 4-F | 93 |
| 13 | F-C₆H₄-CH₂- | CH₃ | CH₃ | CH | — | 164–65 |
| 14 | Cl-C₆H₄-S- | CH₃ | CH₃ | N | 4-Cl | 74–76 |
| 15 | F-C₆H₄-CH₂- | CH₃ | CH₃ | N | — | 102–04 |
| 16 | Cl-C₆H₄-S- | CH₃ | CH₃ | CH | 4-Cl | 94 |
| 17 | 2,3-Cl₂-C₆H₃-O- | CH₃ | CH₃ | CH | 4-Cl | 80–82 |
| 18 | 2,3-Cl₂-C₆H₃-O- | CH₃ | CH₃ | N | 4-Cl | 96–98 |
| 19 | 2-Cl-C₆H₄-O- | CH₃ | CH₃ | N | 4-Cl | 114–16 |
| 20 | 2-Cl-C₆H₄-O- | CH₃ | CH₃ | CH | 4-Cl | 194 |
| 21 | 2-Cl-3-CH₃-C₆H₃-O- | CH₃ | CH₃ | N | 4-Cl | 117 |
| 22 | C₆H₅-O- | CH₃ | CH₃ | N | 4-Cl | 82 |
| 23 | C₆H₅-O- | CH₃ | CH₃ | CH | 4-Cl | 188 |
| 24 | 4-CH₃-C₆H₄-O- | CH₃ | CH₃ | N | 4-Cl | 62 |
| 25 | 4-CH₃-C₆H₄-O- | CH₃ | CH₃ | CH | 4-Cl | 106 |
| 26 | Cl-C₆H₄-O-CH₂- | CH₃ | CH₃ | N | 4-Cl | 104–06 |
| 27 | Cl-C₆H₄-O- | C₂H₅ | CH₃ | N | 4-Cl | 182–84 (× HCl) |
| 28 | F-C₆H₄-CH₂- | CH₃ | CH₃ | N | 4-F | 118 |
| 29 | Cl-C₆H₄-O- | CH₃ | CH₃ | N | 4-F | 82 |
| 30 | F-C₆H₄-O- | CH₃ | CH₃ | N | 4-F | 78 |
| 31 | Cl-C₆H₄-O- | CH₃ | CH₃ | N | 4-F | 154 |
| 32 | F-C₆H₄-O- | CH₃ | CH₃ | N | 4-F | 178 |
| 33 | F-C₆H₄-CH₂- | CH₃ | CH₃ | N | 4-F | 50 |
| 34 | F-C₆H₄-O- | CH₃ | CH₃ | N | 4-F | 114 |
| 35 | Cl-C₆H₄-O- | C₂H₅ | CH₃ | N | 4-F | 66 |
| 36 | 2-F-C₆H₄-O- | CH₃ | CH₃ | N | 4-F | 120 |
| 37 | 2-Cl-C₆H₄-O- | CH₃ | CH₃ | N | 4-F | 147 |

USE EXAMPLES

The compounds shown below are used as comparison substances in the examples which follow:

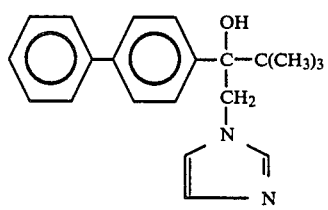

(A)

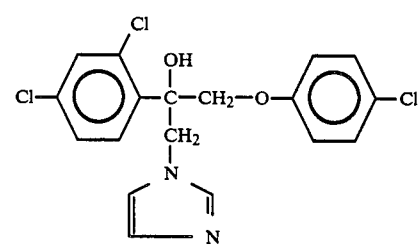

(B)

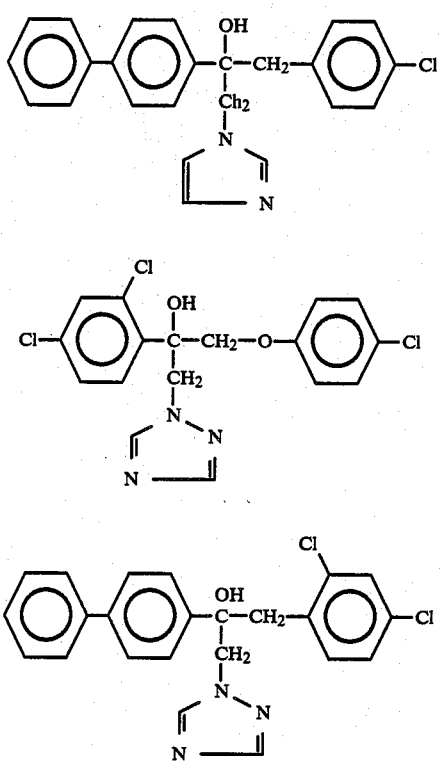

EXAMPLE A

Sphaerotheca test (cucumber)/protective
Solvent: 4.4 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 1, 4, 2, 5, 9, 6, 7, 11, 14 and 18.

TABLE A-continued

Sphaerotheca test (cucumber) / protective

| Active compound | Infestation in % at an active compound concentration | |
|---|---|---|
| | 50 ppm | 5 ppm |
| (9) Cl-C6H4-CH2-C(CH3)2-C(OH)(CH2-triazolyl)-C6H4-F | 13 | |
| (6) Cl-C6H4-CH2-C(CH3)2-C(OH)(CH2-pyrazolyl)-C6H4-F | 10 | |
| (7) Cl-C6H4-CH2-C(CH3)2-C(OH)(CH2-pyrrolyl)-C6H4-Cl | 7 | |
| (11) F-C6H4-CH2-C(CH3)2-C(OH)(CH2-triazolyl)-C6H4-Cl | 10 | |
| (14) Cl-C6H4-S-C(CH3)2-C(OH)(CH2-triazolyl)-C6H4-Cl | 10 | |
| (18) (Cl,Cl)-C6H3-O-C(CH3)2-C(OH)(CH2-triazolyl)-C6H4-Cl | 10 | |

EXAMPLE B

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds according to the following preparation examples: 6 and 7.

TABLE B

*Drechslera graminea* test (barley) / seed treatment (syn. *Helminthosporium gramineum*)

| Active compound | Amount of active compound applied in mg/kg of seed | Diseased plants in % of the total plants emerged |
|---|---|---|
| no dressing | — | 25.5 |
| (B) (known) Cl-C6H4-OCH2-C(OH)(CH2-pyrrolyl)-C6H3(Cl,Cl) | 500 | 23.9 |
| (D) (known) Cl-C6H4-OCH2-C(OH)(CH2-triazolyl)-C6H3(Cl,Cl) | 500 | 20.7 |
| (6) C6H5-CH2-C(CH3)2-C(OH)(CH2-pyrazolyl)-C6H4-F | 500 | 3.7 |
| (7) C6H5-CH2-C(CH3)2-C(OH)(CH2-pyrrolyl)-C6H4-F | 500 | 4.9 |

EXAMPLE C

*Leptosphaeria nodorum* test (wheat)/protective
Solvent: 100 parts by weight of dimethylformamide Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° and a relative atmospheric humidity of about 80%.

Evaluation is effected 10 days after the inoculation.

In this test, a clearly superior activity compared with the prior art is shown, for example, by the compounds according to the following preparation examples: 1, 4, 5 and 3.

TABLE C

*Leptosphaeria nodorum* test (wheat) / protective

| Active compound | Active compound concentration in the spray liquor in % by weight | Disease infestation in % of the untreated control |
|---|---|---|
| (E) (known) 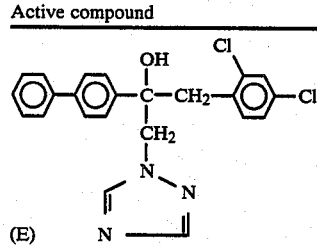 | 0.025 | 78.5 |
| (1) 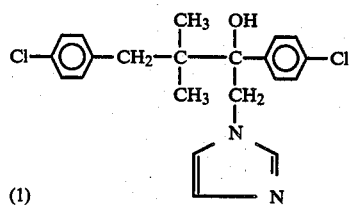 | 0.025 | 16.2 |
| (4) 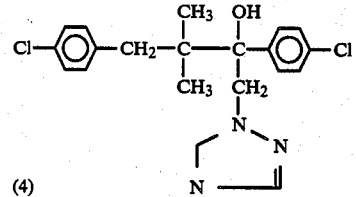 | 0.025 | 16.2 |
| (5) 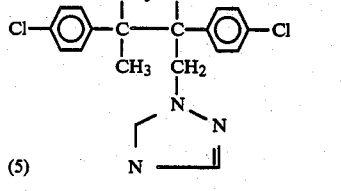 | 0.025 | 37.0 |

TABLE C-continued

*Leptosphaeria nodorum* test (wheat) / protective

| Active compound | Active compound concentration in the spray liquor in % by weight | Disease infestation in % of the untreated control |
|---|---|---|
| (3) 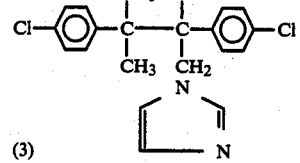 | 0.025 | 37.0 |

EXAMPLE D

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 7, 15, 18 and 19.

TABLE D

Pyricularia test (rice) / protective

| Active compounds | Active compound concentration in % | Disease infestation in % of the untreated control |
|---|---|---|
| (A) (known) 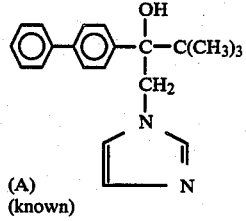 | 0.025 | 100 |
| (7) 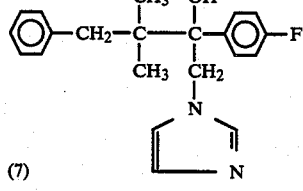 | 0.025 | 25 |

TABLE D-continued

Pyricularia test (rice) / protective

| Active compounds | Active compound concentration in % | Disease infestation in % of the untreated control |
|---|---|---|
| (15) | 0.025 | 25 |
| (18) | 0.025 | 25 |
| (19) | 0.025 | 30 |

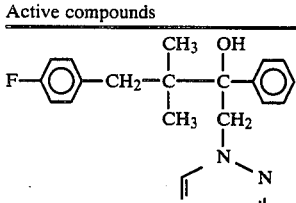

It will be understood that the specification and examples are illustrative but not limitative of the present invention and that other embodiments within the spirit and scope of the invention will suggest themselves to those skilled in the art.

What is claimed is:

1. A method of combating plant-pathogenic fungi which comprises applying to such fungi, to a plant, part of a plant or to a field in which plants are grown or to be grown a fungicidally effective amount of a substituted hydroxyalkyl-azole of the formula

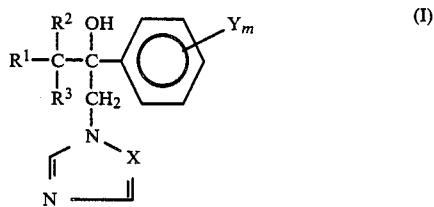

in which
$R^1$ is phenyl, —O-phenyl —S-Phenyl, —SO-phenyl, $SO_2$-phenyl, —$CH_2$-phenyl, —$CH_2$—O-phenyl, —$CH_2$—S-phenyl, —$CH_2$—SO-phenyl or —$CH_2$—$SO_2$-phenyl, in each case optionally mono- or di-substituted by halogen or alkyl with 1 or 2 carbon atoms;
$R^2$ is alkyl with 1 to 4 carbon atoms,
$R^3$ is alkyl with 1 to 4 carbon atoms,
X is a nitrogen atom or the CH group,
Y is halogen, alkyl with 1 to 4 carbon atoms, cycloalkyl with 5 to 7 carbon atoms, alkoxy or alkylthio with in each case 1 to 4 carbon atoms, halogenoalkyl, halogenoalkoxy or halogenoalkylthio with in each case 1 or 2 carbon atoms and 1 to 5 identical or different halogen atoms or phenyl, phenoxy, phenylalkyl or phenylalkoxy with 1 or 2 carbon atoms in the alkyl part or in the alkoxy part, each of which is optionally substituted by halogen or alkyl with 1 or 2 carbon atoms, and m is 0, 1, 2 or 3, or an addition product thereof with an acid or matel salt.

2. The method according to claim 1, in which
$R^1$ is —O-phenyl, —S-phenyl, —SO-phenyl or —$S_2$-phenyl, in each case optionally mono- or di-substituted by fluorine, chlorine or methyl;
$R^2$ is alkyl with 1 to 4 carbon atoms;
$R^3$ is alkyl with 1 to 4 carbon atoms; and
Y is halogen, alkyl with 1 to 4 carbon atoms, cycloalkyl with 5 to 7 carbon atoms, alkoxy or alkylthio with in each case 1 to 4 carbon atoms, halogenoalkyl, halogenoalkoxy or halogenoalkylthio with in each case 1 or 2 carbon atoms and 1 to 5 identical or different halogen atoms, or phenyl, phenoxy, phenylalkyl or phenylalkoxy with 1 or 2 carbon atoms in the alkyl part or in the alkoxy part, each of which is optionally substituted by halogen or alkyl with 1 or 2 carbon atoms.

3. The method according to claim 1, in which
$R^1$ is phenyl, —$CH_2$-phenyl, —$CH_2$—O-phenyl, —$CH_2$—S-phenyl, —$CH_2$—SO-phenyl or —$CH_2$—$SO_2$-phenyl, in each case mono- or di-substituted by fluorine, chlorine or methyl;
$R^2$ is methyl or ethyl;
$R^3$ is methyl or ethyl;
Y is fluorine, chlorine, bromine, methyl, isopropyl, tert.-butyl, cyclohexyl, methoxy, methylthio, trifluoromethyl, trifluoromethoxy or trifluoromethylthio, or phenyl, phenoxy, benzyl or benzyloxy which is optionally substituted by fluorine, chlorine or methyl; and m is 0, 1 or 2.

4. The method according to claim 1, in which
$R^1$ is —O-phenyl, —S-phenyl, —SO-phenyl or —$SO_2$-phenyl, in each case mono- or di-substituted by fluorine, chlorine or methyl;
$R^2$ is methyl or ethyl,
$R^3$ is methyl or ethyl; and
Y is fluorine, chlorine, bromine, methyl, isopropyl, tert.-butyl, cyclohexyl, methoxy, methylthio, trifluoromethyl, trifluoromethoxy or trifluoromethylthio, or phenyl, phenoxy, benzyl or benzyloxy which is optionally substituted by fluorine, chlorine or methyl; and m is 0, 1 or 2.

5. The method according to claim 1, wherin such compound is 2,3-bis-(4-chlorophenyl)-3-methyl-1-(1,2,4-triazol-1-yl)-2-butanol of the formula

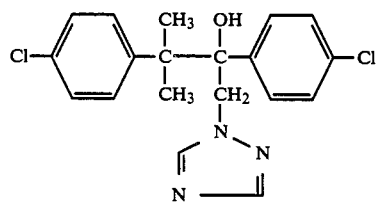

or an addition product thereof with an acid or metal salt.

6. The method according to claim 1, wherein such compound is 2-(4-fluorophenyl)-3,3-dimethyl-4-phenyl-1-(1,2,4-triazol-1-yl)-2-butanol of the formula

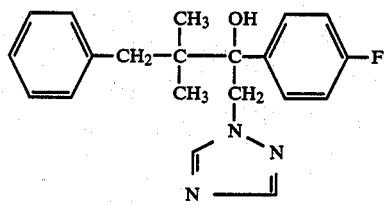

or an addition product thereof with an acid or metal salt.

7. The method according to claim 1, wherein such compound is 2-(4-chlorophenyl)-3-(2,4-dichlorophenoxy)-3-methyl-1-(1,2,4-triazol-1-yl)-2-butanol of the formula

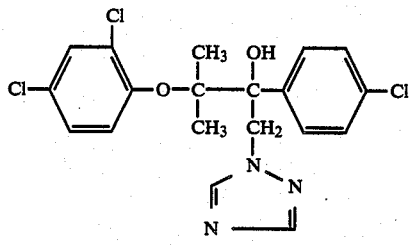

or an addition product thereof with an acid or metal salt.

8. The method according to claim 1, wherein such compound is 2-(4-chlorophenyl)-3-methyl-3-phenoxy-1-(1,2,4-triazol-1-yl)-2-butanol of the formula

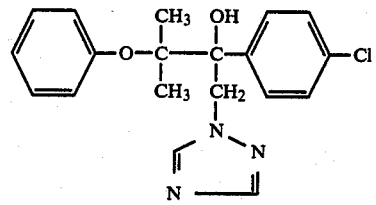

or an addition product thereof with an acid or metal salt.

9. The method according to claim 1, wherein such compound is 3-(4-chlorophenoxy)-2-(4-chlorophenyl)-3-methyl-1-(1,2,4-triazol-1-yl)-2-pentanol of the formula

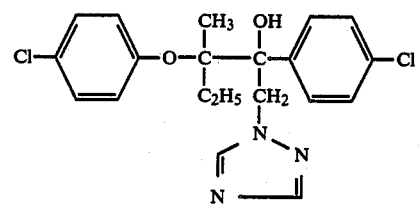

or an addition product thereof with an acid or metal salt.

10. The method according to claim 1, wherein such compound is 3-(2-chlorophenoxy)-2-(4-fluorophenyl)-3-methyl-1-(1,2,4-triazol-1-yl)-2-butanol of the formula

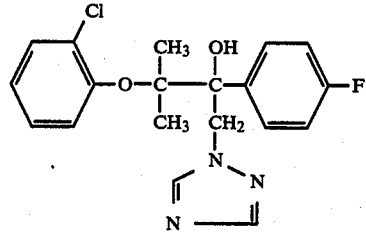

or an addition product thereof with an acid or metal salt.

* * * * *